(12) United States Patent
Hermiston et al.

(10) Patent No.: US 6,764,674 B1
(45) Date of Patent: Jul. 20, 2004

(54) ADENOVIRUS E1B SHUTTLE VECTORS

(75) Inventors: Terry Hermiston, Corte Madera, CA (US); Julie Nye, Berkeley, CA (US)

(73) Assignee: Onyx Pharmaceuticals Inc., Richmond, CA (US)

(*) Notice: Subject to any disclaimer, the term of this patent is extended or adjusted under 35 U.S.C. 154(b) by 0 days.

(21) Appl. No.: 09/472,691

(22) Filed: Dec. 27, 1999

Related U.S. Application Data

(60) Provisional application No. 60/117,814, filed on Jan. 28, 1999, and provisional application No. 60/157,288, filed on Oct. 1, 1999.

(51) Int. Cl.⁷ .......................... A01N 63/00; A61K 48/00
(52) U.S. Cl. .................. 424/93.2; 435/320.1; 435/325; 435/455; 435/235.1; 435/471; 435/358; 435/367; 435/365; 435/456
(58) Field of Search .................... 424/93.2; 435/320.1, 435/455, 325, 471, 456, 235.1, 358, 365, 367; 514/44, 696

(56) References Cited

U.S. PATENT DOCUMENTS

| | | | | |
|---|---|---|---|---|
| 5,643,567 A | * | 7/1997 | Hung et al. | 424/93.2 |
| 5,670,488 A | | 9/1997 | Gregory et al. | |
| 5,856,181 A | | 1/1999 | McCormick | |
| 5,932,210 A | * | 8/1999 | Gregory et al. | 424/93.2 |
| 6,080,578 A | * | 6/2000 | Bischoff et al. | 435/325 |
| 6,328,958 B1 | * | 12/2001 | Amalfitano et al. | 424/93.2 |

FOREIGN PATENT DOCUMENTS

WO    WO 98/46781    10/1998

OTHER PUBLICATIONS

Gomez–Navarro et al., Gene Therapy for Cancer, 1999, European Journal of Cancer, vol. 35 No. 6 pp. 867–885.*

Verma et al. :Gene Therapy—promises, problems and prospects, Nature vol. 389, Sep. 1997, p. 239–242.*

Orkin, et al. :Report and Recommendations of the Panel to Assess the NIH Investment in Research on Gene Therapy, www.nih.gov Dec. 1995.*

WF Anderson, Nature, "Human gene therapy," Apr. 1998, vol. 392, pp. 25–30.*

MJ Mastrangelo et al., Seminars in Oncology, "Gene therapy for Human Cancer: An Essay for Clinicians," Feb. 1996, vol. 23, No. 1, pp. 4–21.*

RG Vile et al., Gene Therapy, "Cancer gene therapy: hard lessons and new courses," 2000, 7, pp. 2–8.*

F Garcia–Sanchez et al., Blood, "Cytosine Deaminase Adenoviral Vector and 5–Fluorocytosine Selectively Reduce Breast Cancer Cells 1 Million–Fold . . . Purging Method for Autologous Transplantation," Jul. 1998, vol. 92, No. 2, pp. 672–682.*

Babiss et al. Journal of Virology 65: 598–605, 1991.*

Hehir et al., "Molecular Characterization of Replication Competent Variants . . . " Journal of Virology, (1996), p. 8459–8467.

Rothmann et al., "Replication of ONYX–015, a Potential Anticancer Adenovirus . . . " Journal of Virology, (1998), p. 9470–9478.

* cited by examiner

Primary Examiner—Scott D. Priebe
Assistant Examiner—Brian Whiteman
(74) Attorney, Agent, or Firm—Gregory Giotta

(57) ABSTRACT

Provided are replication competent, recombinant adenovirus vectors containing mutations in the E1B region which permit the easy deletion of a gene or genes therein, and optionally the substitution therefore of a heterologous gene that substantially exhibits the temporal expression pattern of the E1b region gene(s) deleted. Such vectors have applications for the treatment of disease, and preferably for the treatment of neoplastic disease.

14 Claims, 10 Drawing Sheets

SEQUENCE LISTING

```
<160> NUMBER OF SEQ ID NOS:  12

<210> SEQ ID NO 1
<211> LENGTH: 27
<212> TYPE: DNA
<213> ORGANISM: Oligonucleotide Primer for Adenovirus

<400> SEQUENCE: 1
ggggggtacc tgctggattt tctggcc                                                27

<210> SEQ ID NO 2
<211> LENGTH: 54
<212> TYPE: DNA
<213> ORGANISM: Oligonucleotide Primer for Adenovirus

<400> SEQUENCE: 2
tattctttcc cacccttaag ccacgcccac acatttcagt accagatctg tatc                  54

<210> SEQ ID NO 3
<211> LENGTH: 45
<212> TYPE: DNA
<213> ORGANISM: Oligonucleotide Primer for Adenovirus

<400> SEQUENCE: 3
gttttataaa ggataagtgg agtgaagaaa cccatctgag cgggg                            45

<210> SEQ ID NO 4
<211> LENGTH: 45
<212> TYPE: DNA
<213> ORGANISM: Oligonucleotide Primer for Adenovirus

<400> SEQUENCE: 4
ccccgctcag atgggtttct tcactccact tatcctttat aaaac                            45

<210> SEQ ID NO 5
<211> LENGTH: 72
<212> TYPE: DNA
```

-continued

<213> ORGANISM: Oligonucleotide Primer for Adenovirus

<400> SEQUENCE: 5 gagcccttg gaacccgaga gccggcctgg accctcggga atgaattttg tacaggatcc    60
tgaactgtat cc    72

<210> SEQ ID NO 6
<211> LENGTH: 71
<212> TYPE: DNA
<213> ORGANISM: Oligonucleotide Primer for Adenovirus

<400> SEQUENCE: 6
ggatacagtt caggatcctg tacaaaattc attcccgagg gtccaggccg gctctcgggt    60
tccaagggct c    71

<210> SEQ ID NO 7
<211> LENGTH: 27
<212> TYPE: DNA
<213> ORGANISM: Oligonucleotide Primer for Adenovirus

<400> SEQUENCE: 7
ccgctctaga gaatgcaata gtagtac    27

<210> SEQ ID NO 8
<211> LENGTH: 54
<212> TYPE: DNA
<213> ORGANISM: Oligonucleotide Primer for Adenovirus

<400> SEQUENCE: 8
tattctttcc caccttaag ccacgcccac acatttcagt accagatctg tatc    54

<210> SEQ ID NO 9
<211> LENGTH: 61
<212> TYPE: DNA
<213> ORGANISM: Oligonucleotide Primer for Adenovirus

<400> SEQUENCE: 9
cccaatgcga tttaaatcat aaataaaaaa ccagactctg tttggatttg gatcaagcaa    60
g    61

<210> SEQ ID NO 10
<211> LENGTH: 69
<212> TYPE: DNA
<213> ORGANISM: Oligonucleotide Primer for Adenovirus

<400> SEQUENCE: 10
gcaagacact tgcttgatcc aaatccaaac agagtctggt tttttattat agatttaaat    60
cgcattggg    69

<210> SEQ ID NO 11
<211> LENGTH: 37
<212> TYPE: DNA
<213> ORGANISM: Oligonucleotide Primer for Adenovirus

<400> SEQUENCE: 11
gcgcggatcc gtggaggcta acaatgtcga ataacgc    37

<210> SEQ ID NO 12
<211> LENGTH: 36
<212> TYPE: DNA

-continued

```
<213> ORGANISM: Oligonucleotide Primer for Adenovirus

<400> SEQUENCE: 12
gtgagcattt aaatcagtcg ttcaacgttt gtaatc                                    36
```

ADENOVIRUS E1B SHUTTLE VECTORS

This application claims priority from U.S. Provisional Application Nos. 60/117,814, filed Jan. 28, 1999; and 60/157,288, filed Oct. 1, 1999.

FIELD OF THE INVENTION

This invention relates to adenovirus vectors, and to methods for making and using such vectors. More particularly, this invention relates to improved adenovirus shuttle vectors containing mutations in the E1B region which permit the deletion of the entire region, or select genes therein, and, optionally substitution with a desired heterologous DNA sequence.

BACKGROUND

Adenoviruses are a family of viruses that cause benign respiratory tract infections in humans. Over forty-five serotypes have been identified. Strains 5 and 2 from the C subgroup are two strains that have been used to make vectors because their molecular composition is well characterized, although clinical experience with adenoviral vaccines is with strains 4, 7 and 21 (see, for example, Takafuji, J. Inf. Dis. 140: 48–53 (1979)). Adenoviruses are nonenveloped, icosohedral, double-stranded DNA viruses. The genome is about 36 kb in size and codes for over 40 variously sized polypeptides, including early and late proteins. After binding to a target cell through a capsid fiber protein, the virus is internalized into endosomes, with the capsid eventually escaping relatively intact as it migrates to the nucleus. At the nuclear pore, the capsid dissociates and, the viral DNA moves to the cell nucleus and the early proteins are transcribed, resulting in DNA replication and transcription of the late genes that encode the capsid proteins. Replication occurs in the nucleus of the cell typically, although not exclusively, without integration into the host DNA. New viral particles are assembled in the nucleus and the host cells are lysed, about 36 hours post-infection, releasing the virus. Adenoviruses infect a broad range of cell types and transduction has been observed in replicating and in nonreplicating cells.

In recent years, human adenoviruses have become popular as vehicles for gene transfer into mammalian cells because the virus uses the machinery of the host cell to synthesize viral DNA, RNA and proteins and because gene transcription, genomic organization and the identity of the DNA in adenovirus have been well defined. Adenoviral vectors are known and their use facilitates the study of protein function in mammalian cells and permits production of gene products. In addition, adenoviral vectors may be used as recombinant viral vaccines. The usual method of making an adenoviral vector is to substitute the E1 region of the viral genome with a transgene driven by a selected exogenous promoter, normally containing a strong enhancer. Substitutions and/or deletions have also been made in the E3 and E4 regions. Substitutions in the E1 region are particularly advantageous because the E1 proteins have oncogenic and lytic properties.

Modification of the viral genome can be accomplished by employing recombination or by employing molecular biological techniques. The latter approach typically takes advantage of a single Cla-1 site at the left end of the adenovirus strain 5 ("Ad-5") genome that disrupts the E1A region, and the left terminal sequences necessary for encapsidation and containing an origin of replication, about 900 basepairs of the 5' end of the genome. A plasmid expression vector is also constructed having a single Cla-1 site downstream of the desired transgene and a copy of the adenovirus terminal sequences upstream. This vector is cut and ligated to the E1 negative adenoviral fragment and transfected into human 293 kidney cells immortalized by the constitutive expression of E1A and E1B proteins, to provide E1 functions in trans. Plaques are selected and screened for recombinants, repurified and then used to generate bulk stock of purified recombinant adenoviral vector. Yields can be as high as $10^{12}$ to $10^{13}$ particles/mL. See Stratford-Perricaudet, J. Clin. Invest. 90: 626–30 (1992). However, this approach poses several problems, which are discussed in PCT Patent Publication No. WO 96/25507, published Aug. 22, 1996 (International Application No. PCT/US96/02336).

In another approach, foreign genes are inserted into the E1 region (see McGrory, Virology 163: 614–17 (1988)), into the E3 region (see Hanke, Virology 177: 437–44 (1990) and Bett, J. Virol. 67: 5911–21 (1993)) or into the E3 region of an E1 deleted vector. Briefly, this approach employs replacement of adenoviral genomic DNA sequences with another DNA fragment to create a plasmid containing a genomic sequence which exceeds the packaging limit of the adenovirus virions. The "construct" can then be propagated as a plasmid (pJM17), which can be rescued as infectious virions when the foreign fragment is replaced by homologous recombination with another DNA fragment small enough to permit packaging. For additional general information on these vectors and their uses see, Hitt, *Construction and propagation of human adenovirus vectors*. In: Cell Biology: a Laboratory Handbook, J. Celis (ed), Academic Press, N.Y, 1995; see Graham, *Adenovirus based expression vectors and recombinant vacines*. In: Vaccines: New Approaches to Immunological Problems. R. W. Ellis (ed), Butterworth, pp 363–390, 1992 and see Graham, *Manipulation of adenovirus vectors*. In: Methods in Molecular Biology, Vol. 7: Gene Transfer and Expression Techniques. E. J. Murry and J. M. Walker (eds) Humana Press Inc., Clifton, N.J., pp 109–128, 1991.

The originally designed and constructed adenovirus vectors reduced virus replication by deleting or mutating portions of the E1A and E1B region. The disadvantage to this approach was that packaging into viral capsids was inefficient, due to the increase in genome size from the addition of the transgene, and the viral stock titer was concomitantly reduced. Deletions in the E3 region increased the amount of heterogeneous DNA which could be inserted into the vector, but it was believed that expression of the E3 gene was needed to assist virus infected cells in avoiding the host immune response.

Thus, it would be advantageous to provide an improved adenovirus vector permitting large insertions of heterogeneous DNA without sacrificing packaging efficiency or protective immunity.

SUMMARY OF THE INVENTION

In one aspect, the invention provides methods for constructing replication competent, adenoviral shuttle vectors that can have one or more genes in the E1B region deleted, the vectors so constructed, and optionally heterologous genes of interest substituted for the deleted genes which allows for the temporal expression of the heterologous genes in a manner similar to the endogenous adenoviral gene it replaces.

In a second aspect, the invention provides an E1B shuttle vector wherein the 55K adenoviral gene can be deleted and a heterologous gene of interest substituted therefore.

In another aspect, the invention provides an E1B shuttle vector wherein the E1B region genes, 19K, and 55K can be deleted, and a heterologous gene of interest substituted therefore.

In another aspect, the invention provides an E1B shuttle vector wherein either the 19K, 55K and pIX genes can be deleted, or the pIX gene can be deleted, and a heterologous gene of interest substituted therefore.

In a further aspect of the invention, the E1B shuttle vectors may express a heterologous gene, which expression is preferably driven by the endogenous E1B promoter, wherein the gene encodes a cytokine, including the interleukins, tumor necrosis factor alpha, interferon gamma, or cell cycle regulatory proteins, including p16, or ras, or proteins that induce cellular suicide, or apoptosis, or prodrug activators, including cytosine deaminase or thymidine kinase, or a chemokine including macrophage inhibitory proteins (mip), including mip-3 alpha. The temporal expression pattern of the heterologous gene is similar to the endogenous adenoviral gene it replaces.

In yet another aspect of the invention, E1B shuttle vectors are described wherein such vectors also have mutations elsewhere in the adenoviral genome, preferably in the E1A, E3 and/or E4 regions.

In another aspect of the invention, methods are described wherein the invention E1B shuttle vectors are used for the beneficial treatment or prevention of disease.

In a further aspect of the invention, E1B shuttle vectors may be administered to a patient in a therapeutically effective amount and in a pharmaceutically acceptable carrier. These and other objects of the present invention will become apparent to one of ordinary skill in the art upon reading the description of the various aspects of the invention in the following specification. The foregoing and other aspects of the present invention are explained in greater detail in the drawings, detailed description, and examples set forth below.

DETAILED DESCRIPTION OF THE INVENTION

Figure 1:
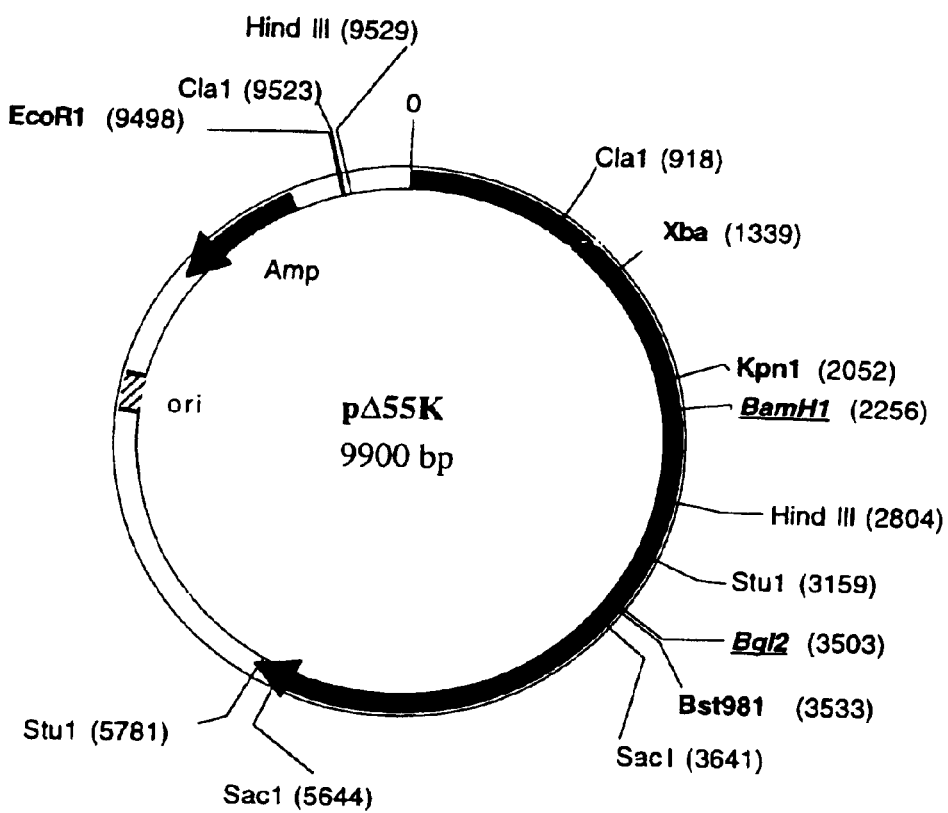
FIG. 1 shows the restriction map of the plasmid pΔ55K.

All publications, including patents and patent applications, mentioned in this specification are herein incorporated by reference to the same extent as if each individual publication was specifically and individually indicated to be incorporated by reference in its entirety.

Definitions

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., *Molecular Cloning: A Laboratory Manual*, 2nd. edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

Those skilled in the art will also recognize publications that facilitate genetic engineering of the invention adenovirus to produce the invention E1b shuttle vectors. Such would include the work of Hitt, M., et al Construction and propagation of human adenovirus vectors. In: Cell Biology: a Laboratory Handbook; J. Celis (Ed), Academic Press, N.Y. (1996); Graham, F. L. and Prevec, L. Adenovirus based expression vectors and recombinant vaccines. In: Vaccines: New Approaches to Immunological Problems. R. W. Ellis (ed) Butterworth. Pp. 363–390; and Graham, F. L. and Prevec, L. Manipulation of adenovirus vectors. In: Methods in Molecular Biology, Vol. 7: Gene Transfer and Expression Techniques. E. J. Murray and J. M. Walker (eds) Humana Press Inc., Clifton, N.J. pp 109–128, 1991. The materials and methods described in these articles were or could be used below.

In the formulae representing selected specific embodiments of the present invention, the amino- and carboxy-terminal groups, although often not specifically shown, will be understood to be in the form they would assume at physiological pH values, unless otherwise specified. Thus, the N-terminal $H_2^+$ and C-terminal-$O^-$ at physiological pH are understood to be present though not necessarily specified and shown, either in specific examples or in generic formulas. In the polypeptide notation used herein, the lefthand end of the molecule is the amino terminal end and the righthand end is the carboxy-terminal end, in accordance with standard usage and convention. Of course, the basic and acid addition salts including those which are formed at nonphysiological Ph values are also included in the compounds of the invention. The amino acid residues described herein are preferably in the "L" isomeric form. Stereoisomers (e.g., D-amino acids) of the twenty conventional amino acids, unnatural amino acids such as a,a-distributed amino acids, N-alkyl amino acids, lactic acid, and other unconventional amino acids may also be suitable components for polypeptides of the present invention, as long as the desired functional property is retained by the polypeptide. For the peptides shown, each encoded residue where appropriate is represented by a three letter designation, corresponding to the trivial name of the conventional amino acid, in keeping with standard polypeptide nomenclature (described in *J. Biol. Chem.*, 243:3552–59 (1969) and adopted at 37 CFR §1.822 (b)(2)). Free functional groups, including those at the carboxy- or amino-terminus, referred to as non-interfering substituents, can also be modified by amidation, acylation or other substitution, which can, for example, change the solubility of the compounds without affecting their activity. As employed throughout the disclosure, the following terms, unless otherwise indicated, shall be understood to have the following meanings:

The term "isolated protein" referred to herein means a protein of cDNA, recombinant RNA, or synthetic origin or some combination thereof, which by virtue of its origin the "isolated protein" (1) is not associated with proteins found in nature, (2) is free of other proteins from the same source, e.g. free of human proteins, (3) is expressed by a cell from a different species, or (4) does not occur in nature.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "adenovirus" as referred to herein indicates over 47 adenoviral subtypes isolated from humans, and as many from other mammals and birds. See, Strauss, "Adenovirus infections in humans," in *The Adenoviruses*, Ginsberg, ed., Plenum Press, New York, N.Y., pp. 451–596 (1984). The term preferably applies to two human serotypes, Ad2 and Ad5.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like known in the art. As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, b-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "sequence homology" referred to herein describes the proportion of base matches between two nucleic acid sequences or the proportion amino acid matches between two amino acid sequences. When sequence homology is expressed as a percentage, e.g., 50%, the percentage denotes the proportion of matches over the length of sequence that is compared to some other sequence. Gaps (in either of the two sequences) are permitted to maximize matching; gap lengths of 15 bases or less are usually used, 6 bases or less are preferred with 2 bases or less more preferred.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as may be used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

The term "polypeptide fragment" or "peptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically 8–10 amino acids long, preferably at least 10–20 amino acids long, and even more preferably 20–70 amino acids long.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference.

The production of proteins from cloned genes by genetic engineering is well known. See, e.g. U.S. Pat. No. 4,761,371 to Bell et al. at column 6, line 3 to column 9, line 65. The discussion which follows is accordingly intended as an overview of this field, and is not intended to reflect the full state of the art.

DNA which encodes proteins that may be inserted into the adenoviral constructs of the instant invention can be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from known gene sequence information. Probes may be labeled with a detectable group such as a fluorescent group, a radioactive atom or a chemiluminescent group in accordance with known procedures and used in conventional hybridization assays, as described in greater detail in the Examples below.

In the alternative, a gene sequence may be recovered by use of the polymerase chain reaction (PCR) procedure. See U.S. Pat. No. 4,683,195 to Mullis et al. and U.S. Pat. No. 4,683,202 to Mullis.

A vector is a replicable DNA construct, and are used either to amplify DNA encoding a hi desired protein and/or to express DNA which encodes the protein. An expression vector is a as replicable DNA construct in which a DNA sequence encoding a protein of interest is operably linked to suitable control sequences capable of effecting the expression of the protein in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the vectors constructed using recombinant DNA techniques.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading frame. A preferred embodiment promoter of the instant invention in those instances where certain E1b region DNA is deleted and foreign DNA substituted therein is expression of the foreign DNA from the endogenous E1B promoter. It will also be appreciated that a tissue specific promoter which is operably linked to the foreign DNA may be employed.

Suitable host cells include prokaryotes, yeast cells, or higher eukaryotic cells. Prokaryotes include gram negative or gram positive organisms, for example *Escherichia coli* (*E. coli*) or Bacilli. Higher eukaryotic cells include established cell lines of mammalian origin as described below. Exemplary host cells are DH5a, *E. coli* W3110 (ATCC 27,325), *E coli* B, *E. coli* X 1776 (ATCC 31,537) and *E. coli* 294 (ATCC 31,446).

A broad variety of suitable microbial vectors are available, and may have applications in constructing the instant adenoviral vectors. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., *Gene* 2, 95 (1977). pBR322 contains genes for ampicillin and tetracycline resistance and thus provides easy means for identifying transformed cells. Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., Nucleic Acids Res. 8, 4057 (1980) and EPO Application Publication Number 36,776) and the tac promoter (H. De Boer et al., Proc. Natl. Acad. Sci. USA 80, 21 (1983)). While these are commonly used, other microbial promoters are suitable. Details concerning nucleotide sequences of many promoters have been published, enabling a skilled worker to operably ligate them to DNA in plasmid or viral vectors (Siebenlist et al., *Cell* 20, 269, 1980)).

Cultures of cells derived from multicellular organisms are a desirable host for recombinant protein synthesis. In principal, any higher eukaryotic cell culture is workable, whether from vertebrate or invertebrate culture. However, mammalian cells are preferred. Propagation of such cells in cell culture has become a routine procedure. See Tissue Culture, Academic Press, Kruse and Paterson, editors (1973). Examples of useful host cell lines are VERO and HeLa cells, Chinese hamster ovary (CHO) cell lines, and FL5.12, WI138, BHK, COS-7, CV, and MDCK cell lines.

Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

The transcriptional and translational control sequences in expression vectors to be used in transforming vertebrate cells are often provided by viral sources. A variety of viral and mammalian constitutive promoter elements can be used. See, Mittal et al., (1993) Virus Research, vol. 28, pp. 67–90. For example, commonly used promoters are derived from polyoma, CMV, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978).

E1B Shuttle Vector Construction

The present invention provides novel, replication competent, adenoviral shuttle vectors having unique cloning sites in the E1B region which permit selective deletion of the following genes, or groups of genes: 55K; 19K and 55K; 19K, 55K, pIX; and pIX.

A preferred embodiment of the invention is the retention of the endogenous E1B promoter which favors the expression of heterologous genes inserted in the E1B shuttle vectors.

To generate the E1B shuttle vectors described herein, the following strategy may be adopted using an appropriate plasmid containing the adenovirus genome. The preferred plasmid is pXC1, obtainable from Microbix Biosystems, Toronto, Canada. See, also the Microbix Biosystems technical description "Gene Transfer with Adenovirus Vectors." While pXCI was used as starting material to produce the invention E1B shuttle vectors, any adenovirus vector known in the art may be employed if it contains the following elements: beginning at the 5' end, an adenoviral 5' ITR (inverted terminal repeat), an adenoviral encapsidation signal and an E1A enhancer sequence, a promoter sequence, an adenoviral promoter or a foreign promoter, a tripartite leader sequence, a poly A signal and a DNA segment that corresponds to a segment of the adenoviral genome.

To generate the invention E1B shuttle vectors, the Bgl II and Bam HI restriction sites, nucleotides 3328 and 9875, respectively, were removed from pXC1 in order to create unique Bgl II and Bam HI restriction sites that facilitate removal of the desired E1B genes. This plasmid is referred to herein as ΔBam/Bgl pXC1.

Using ΔBam/Bgl pXC1, an E1B shuttle vector that permits removing both the 19K and 55K genes, and optionally substituting a heterologous gene, can be generated by disrupting the initiator methionine codon for the E1B-19K gene by creating a novel restriction site, and a second restriction site upstream of the E1B-55K stop codon. The preferred restriction sites are, as referred to above, BamHI and Bgl II. This plasmid is referred to as pΔE1B.

Using ΔBam/Bgl pXC1, an E1B shuttle vector that permits removing the 55K gene, and optionally substituting a heterologous gene, while retaining the E1B-19K gene, can be generated by mutating the 55K gene initiation codon and additionally incorporating a stop codon in the E1B-55k gene coding sequence, at preferably the third amino acid, and creating a second restriction site upstream of the E1B-55K stop codon, as in the ΔE1B vector. Neither mutation, the mutation in the initiation codon nor the stop codon, alter the amino acid sequence in the overlapping E1B-19K coding sequence. This plasmid is referred to as pΔE1B-55K.

Using pΔE1B, the plasmid pΔE1B/pIX may be created, which allows for removal of the pIX gene, and optionally substituting a heterologous gene therein, while retaining the E1B-19K and 55K genes, or E1B-19K and a portion of the 55K gene, or the entire E1B region can be removed, that is all three genes: 19, 55K and pIX. The preferred method whereby this plasmid is constructed is the introduction of a unique Swa 1 restriction site at the stop codon for pIX.

The preferred method to construct an adenoviral E1B shuttle vector containing heterologous DNA encoding a polypeptide sequence is to contact the plasmid shuttle vectors with an unpackageable, circular, adenoviral Ad 5 genomic plasmid under conditions suitable for homologous recombination. The adenoviral vector produced thereby is isolated in the form of infectious viral particles. The adenoviral Ad5 genomic plasmid is preferably pJM17, pBHGE3, pBHG10 or pBHG11, or a derivative thereof. For additional information on these vectors and their uses see, Hitt, *Construction and propagation of human adenovirus vectors*. In: Cell Biology: a Laboratory Handbook, J. Celis (ed), Academic Press, N.Y, 1995; see Graham, *Adenovirus based expression vectors and recombinant vacines*. In: Vaccines: New Approaches to Immunological Problems. R. W. Ellis (ed), Butterworth, pp 363–390, 1992 and see Graham, *Manipulation of adenovirus vectors*. In: Methods in Molecular Biology, Vol. 7: Gene Transfer and Expression Techniques. E. J. Murry and J. M. Walker (eds) Humana Press Inc., Clifton, N.J., pp 109–128, 1991.

In the above-described embodiments, the adenoviral shuttle vector constructs may additionally comprise an origin of replication, a nucleotide sequence encoding a selectable marker and/or a heterologous DNA encoding a polypeptide sequence inserted between the BamHI and Bgl II restriction endonuclease sites or between the Swa1 and the BamHI restriction endonuclease sites. Preferred polypeptide sequences, or fragments thereof that encode biologically active peptides, include those that encode immunomodulatory proteins, and pro-drug activators (i.e. cytosine deaminase, thymidine kinase, U.S. Pat. Nos. 5,358,866, and 5,677,178). Examples of the former would include interleukin 2, U.S. Pat. Nos. 4,738,927 or 5,641,665; interleukin 7, U.S. Pat. Nos. 4,965,195 or 5,328,988; and interleukin 12, U.S. Pat. No. 5,457,038; tumor necrosis factor alpha, U.S. Pat. Nos. 4,677,063 or 5,773,582; interferon gamma, U.S. Pat. Nos. 4,727,138 or 4,762,791; or GM-CSF, U.S. Pat. Nos. 5,393,870 or 5,391,485. Additional immunomodulatory proteins further include macrophage inflammatory proteins, including MIP-3 alpha, (See, Well, T. N. and Peitsch, M C. J. Leukoc. Biol vol 61 (5): pages 545–50, 1997). Any selectable marker known in the art may be employed.

The preferred promoter for expressing heterologous genes inserted in an E1B shuttle vector is the E1B endogenous promoter. However, the E1B shuttle vectors can incorporate a tissue specific promoter. An example of a tissue specific promoter includes the prostate specific antigen promoter. See, PCT/US95/14461, or U.S. Pat. No. 5,648,478.

A desired heterologous DNA sequence, typically containing a heterologous gene, may be inserted into the cloning site to produce a plasmid vector, which is then used to produce an adenoviral vector by homologous recombination with a modified adenovirus in which one or more native transcriptional regulatory sequences have been deleted and replaced with the desired transcriptional regulatory sequence.

While a heterologous gene can be substituted for any of the three E1b genes, the preferred region for substitution is 55K. One reason this region is preferred is that the presence of a suitable heterologous gene with anti-tumor activity will confer on the virus enhanced anti-tumor activity over that exerted by the virus alone. It is known that adenovirus that have deletions or mutations in E1b, and thus cannot express 55K, confer on the virus the ability to preferentially replicate in cells that are functionally defective in the tumor suppressor, p53 compared to normal cells. Certain neoplastic cells are, or can become defective in p53 function in numerous ways, including a defect in those proteins that interact with p53; that is, a defect in the p53 pathway that renders p53 functionally inactive. Included within the definition of neoplastic cells are cells that lack p53 function, but are not frankly neoplastic. See, U.S. Pat. No. 5,677,178. Examples of cells in the later category would be cells associated with Barrett's syndome, or leukoplakia. Indeed, the instant invention vectors have applications for a spectrum of diseases resulting from the functional inactivation of p53. Thus, an E1b shuttle vector of the instant invention that is deleted in 55K, or that has substituted therefore a heterologous protein with anti-neoplastic cell activity will be effective for the treatment of neoplasia. Such shuttle vectors, with or without a heterologous gene, will also have applications for the treatment of other medical conditions in which the tumor suppressor p53 is functionally inactive.

A preferred heterologous gene with anti-cancer activity is cytosine deaminase, and it may be preferably inserted into either pΔE1B to create pΔE1B/CD, or in pΔE1B-55K to create pΔE1B-55K/CD. From these plasmids, the corresponding viruses are readily generated by co-transfecting 293 cells with the adenovirus right end vector pJM17, using the standard phosphate procedure. The resulting viruses are referred to herein as ΔE1B/CD and ΔE1B55K/CD. The virus ΔE1B55K/CD is useful as a means for preferably killing cells that lack p53 function, including tumor cells, in that the virus will exert both viral cytopathic effects that are enhanced by the effect of cytosine deaminase in the presence of 5-fluorocytosine. Cytosine deaminase converts 5-fluorocytosine (5FC) to 5-fluorouracil (5FU) and 5FU is toxic to mammalian cells. See, U.S. Pat. Nos. 5,624,830 and 5,358,866.

Propagation of Mutant Adenovirus

Adenoviral mutants of the invention typically are propagated as viral stocks in a cell line (e.g., the 293 cell line ATCC # CRL 1573, American Type Culture Collection, Rockville, Md.; Graham et al. (1977) *J. Gen. Virol.* 36: 59, or A549 cells) which can provide certain desired viral functions, if needed, in trans to support replication and formation of infectious mutant virions. Human 293 cells, which are human embryonic kidney cells transformed with adenovirus E1A/E1B genes, typify useful permissive cell lines. Other cell lines that allow replication-deficient adenoviral vectors to propagate can be used, for example, HeLa cells.

Formulations

Pharmaceutical compositions are also included as a aspect of the invention. Such pharmaceutical compositions comprise an adenoviral vector construct of the invention in a therapeutically effective amount and a pharmaceutically acceptable carrier. The term "pharmaceutically acceptable" means a material that does not interfere with the effectiveness of the biological activity of the active ingredients and that is not toxic to the host to which it is administered. A pharmaceutically acceptable carrier may contain or comprise a physiologically acceptable compound that acts to stabilize the composition or to increase or decrease the absorption of the active ingredient. Such a compound can include for example carbohydrates such as glucose, sucrose or dextrans, antioxidants such as ascorbic acid or glutathione, chelating agents, low molecular weight proteins or other stabilizers or excipients. Other acceptable compounds include wetting agents, emulsifying agents, dispersing agents or preservatives such as phenol and ascorbic acid. The skilled artisan is aware that choice of a pharmaceutically acceptable carrier depends on route of administration and on the particular physiochemical characteristics of the active ingredient. Examples of carriers, stabilizers or adjuvants can be found in Martin, *Remington's Pharm Sci*, 15$^{th}$ ed. (Mack Publ Co, Easton, 1975).

The vectors of the invention should preferably be formulated in solution at neutral pH, about 6.5 to about 8.5, more preferably about 7 to 8, with an excipient to bring the solution to isotonicity, for example mannitol or sodium chloride, pH buffered with art-recognized buffer solutions. The amount of active ingredient will depend upon the severity of the condition, the route of administration, the age and weight of the patient and the patient's physical condition, the biological activity of the active ingredient, and ultimately will be decided by the attending physician or medical professional. It is currently contemplated that the pharmaceutical composition should contain about $10^3$ to about $10^5$ viral particles, preferably about $10^{11}$ viral particles. In practicing the method or treatment of the invention, a therapeutically effective amount of the vector is administered to a mammal. By therapeutically effective amount, we mean the total amount of each active ingredient of the composition that is sufficient to show a meaningful patient benefit. When applied to an individual active ingredient, administered alone, the term refers to that ingredient alone. When applied to a combination, the term refers to combined amounts of the active ingredients that result in the therapeutic effect, whether administered in combination, serially or simultaneously. Modes of administering a pharmaceutical containing the vector of the invention are well known in the art and include, for example, oral administration, intratumor administration and intravenous, intramuscular or intraperitioneal administration.

Adenoviruses of the invention, or the DNA contained therein, may be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions are encapsulated in liposomes or immunoliposomes. For example, a suspension of adenovirus virions can be encapsulated in micelles to form immunoliposomes by conventional methods (U.S. Pat. No. 5,043,164, U.S. Pat. No. 4,957,735, U.S. Pat. No. 4,925,661; Connor and Huang (1985) *J. Cell Biol.* 101: 582; Lasic D D (1992) *Nature* 355: 279; *Novel Drug Delivery* (eds. Prescott L F and Nimmo W S: Wiley, New York, 1989); Reddy et al. (1992) *J. Immunol.* 148: page 1585). Immunoliposomes comprising an antibody that binds specifically to a cancer cell antigen (e.g., CALLA, CEA) present on the cancer cells of the individual may be used to target virions, or virion DNA to those cells.

Single or multiple administrations of the compositions can be carried out with dose levels and pattern being selected by the treating physician. In any event, the pharmaceutical formulations should provide a quantity of the antineoplastic adenoviruses of this invention sufficient to effectively treat the patient.

Antineoplastic adenoviral therapy of the present invention may be combined with other antineoplastic protocols, such as conventional chemotherapy, or radiation. In the event a particular adenoviral mutant provokes an immune response that dampens the effectiveness of the virus, administration of immunosuppressive drugs, including the appropriate antibody, may be performed.

Uses of the Invention

It will be apparent, based on the discussion above, that the adenoviral vectors/viruses described herein have multiple uses including applications in gene therapy. For example, in one embodiment of the invention, a gene that encodes a medically useful protein may be cloned into the E1B region of the instant invention virions, and the virions used directly in gene therapy protocols to treat disease. In another embodiment of the invention, discussed above, such mutant virions may have deletions in the E1B that encodes the 55K protein, and have substituted therefore a gene with medically beneficial properties. Such genes might encode cytokines, including the interleukins, cell cycle regulatory proteins, including p16, or ras, or proteins that induce cellular suicide, or apoptosis, prodrug activators, including cytosine deaminase or thymidine kinase. Further, tumor necrosis factor alpha, interferon gamma, and mip-3 alpha may be utilized.

The instant adenoviral vectors may also be used to express proteins that are useful immunogens, or as a vaccine, and to transform cells which do not ordinarily express a particular protein to thereafter express this protein. Cells expressing these molecules are useful as intermediates for making cell membrane preparations useful for binding assays, which are in turn useful for drug screening.

The mutations in the E1 region described herein may be incorporated into adenoviral mutants that have mutations outside the E1B region. Preferably such mutations would be in the E1a region of the adenoviral genome. In this case, the preferred E1a mutations would confer on the E1B shuttle vector the ability to preferentially replicate in neoplastic cells compared to normal cells, wherein the neoplastic cells are functionally defective in the retinoblastoma tumor suppressor gene product, or p105 Rb. Such inactivating mutations typically occur in the E1a CR1 domain (amino acids 30–85 in Ad5: nucleotide positions 697–790) and/or the CR2 domain (amino acids 120–139 in Ad5; nucleotide positions 920–967), which are involved in binding the p105 RB protein. Defective Rb can arise in numerous ways, including a defect in those proteins that interact with Rb; that is, a defect in the Rb pathway that renders Rb functionally inactive. See, U.S. Pat. No. 5,677,178. Thus, the E1b adenoviral mutations described herein could be combined, for example, with the E1a deletion in the adenovirus Ad5 NT dl 1010. The most preferred E1B shuttle vector with an E1a deletion would also have E1b 55K substituted with a heterologous DNA that encodes a protein with anti-neoplastic cell activity. This vector would preferentially kill neoplastic cells that are functionally p53 and/or Rb defective, with enhanced anti-cancer activity arising from the protein encoded by the heterologous DNA.

The Examples which follow are illustrative of specific embodiments of the invention, and various uses thereof. They are set forth for explanatory purposes only, and are not to be taken as limiting the invention.

EXAMPLES

General Methods

Methods for the construction and propagation of human adenovirus vectors are known in the art and will be understood to be applied in the Examples presented below by the skilled practitioner of the art. Such would include the work of Hitt, M., et al Construction and propagation of human adenovirus vectors. In: Cell Biology: a Laboratory Handbook; J. Celis (Ed), Academic Press, N.Y. (1996); Graham, F. L. and Prevec, L. Adenovirus based expression vectors and recombinant vaccines. In: Vaccines: New Approaches to Immunological Problems. R. W. Ellis (ed) Butterworth. Pp. 363–390; and Graham, F. L. and Prevec, L. Manipulation of adenovirus vectors. In: Methods in Molecular Biology, Vol. 7: Gene Transfer and Expression Techniques. E. J. Murray and J. M. Walker (eds) Humana Press Inc., Clifton, N.J. pp 109–128, 1991. The materials and methods described in these articles were or could be used below.

Example 1

Plasmid Construction

ΔBam/BglpXCI.

Plasmid pXCI (obtainable from Microbix Biosystems, Toronto, Canada. See, also the Microbix Biosystems technical description "Gene Transfer with Adenovirus Vectors") was used as starting material. The single restriction endonuclease sites for Bgl II (nucleotide 3328) and BamHI (nucleotide 9875) were removed from pXCI by restriction endonuclease digestion and filled in with T4 DNA polymerase (Boehringer Mannheim, Indianapolis, Ind.) as described by Boehringer Mannheim in the product description. This modified plasmid served as the template for the creation of the E1B shuttle vectors pΔE1B, pΔE1B-55K, and pΔE1B/pIX as follows.

A. Creation of Vector pΔE1B.

Using ΔBam/BglpXC1 as the template, a Bam HI linker (New England Biolabs, is NEB#1071) was inserted into the EcoNI site at nucleotide 1715, which disrupts the initiator methionine codon for the E1B-19K gene, following an EcoNI partial restriction digest and fill in reaction using T4 DNA polymerase. This intermediate construct called BampXC1 was used as the template to create a unique BglII at nucleotide 3503, four base pairs upstream of the E1B-55K stop codon. The BglII site was engineered using the Clonetech Advantage Kit (Clonetech) and the primers:
E1BKpn-C:
5'$_{2045}$GGGGGGTACCTGCTGGATTTTCTGGCC$_{2070}$ (SEQ ID NO. 1) Bst981-NC:
5'$_{3552}$TATTCTTTCCCACCCTTAAGCCACGC-CCACACATTTCAGTACC<u>AGATCT</u>GTATC$_{3498}$ (SEQ ID NO. 2)
The bold and underlined portion of the above sequence indicates the Bgl II site added beginning at nucleotide 3503. Following mutagenesis, a Kpn I-Bst98I fragment (which contains the newly created Bgl II sites) was isolated and cloned back into ΔBampXC1 to create the pΔE1B plasmid. The E1B region was subsequently sequenced to confirm the mutations. The BamHI and Bgl II sites can be used to clone in heterologous gene of interest into the E1B region replacing both the 19K and 55K genes. See FIG. 1.

B. Creation of Vector pΔE1B-55K.

The ΔBam/BglpXC1 plasmid was also modified to allow for substitution of the E1B-55K gene coding sequences while retaining the E1B-19K coding sequences, as follows. Using Stratagenes' "Quick Change Site-Directed Muatagenisis Kit", the following mutations were introduced.

1. The E1B-55K gene initiator methionine was modified, using the primers D55Kmet-C:
5'$_{2002}$GTTTTATAAAGGATAA<u>G</u>TGGAG <u>T</u>GAAGAAACCCATCTGAGCGGGG$_{2047}$ (SEQ ID NO. 3) D55Kmet-NC:
5'$_{2047}$CCCCGCTCAGATGGGTTTCTTC<u>A</u>CTCCA <u>C</u>TTATCCTTTATAAAAC$_{2002}$ (SEQ ID NO. 4)
The nucleotides that are bold and underlined in the above sequences differ from the wild type sequence. These nucleotide alterations change the initiation-codon for the E1B-55K gene to a valine and also place a stop codon in the E1B-55K coding sequence, at the third amino acid, identical to that of adenovirus dl1520 (See, Barker and Berk, 1987, and U.S. Pat. No. 5,677,178). These mutations do not alter the amino acid sequence in the overlapping E1B-19K coding sequence. Mutations were screened by sequencing, and the intermediate plasmid was termed Δ55Kmet.

2. Using Δ55Kmet as the template, a BamHI site was created directly downstream of the E1B 19K coding sequence using the oligonucleotides:
E1B-71C:
5'$_{2202}$GAGCCCC <u>T</u>TGGAACCCGAGAGCCGGCCTGGACCCTCGGG AATGAAT<u>T</u>TTGTACAGG <u>AT</u>CCTGAACTGTATCC$_{2272}$ (SEQ ID NO. 5) E1B-71NC:
5'$_{2272}$GGATACAGTTCAGG<u>AT</u>CCTGTACAA <u>A</u>ATTCATTCCCGAGGGTCCAGGCCGGCTCTCG GGTTCCA<u>A</u>GGGCTC$_{2202}$ (SEQ ID NO. 6)
The underlined and bold nucleotides in the above sequences alter potential in-frame initiator methionines in the E1B-55K coding sequence and introduce a unique Ban HI restriction enzyme site 11 bp downstream of the E1B-19K stop codon. Confirmation of mutagenisis was done by restriction digestion with BamHI. The intermediate was termed Δ55Kmet3'BamHI.

Figure 2:
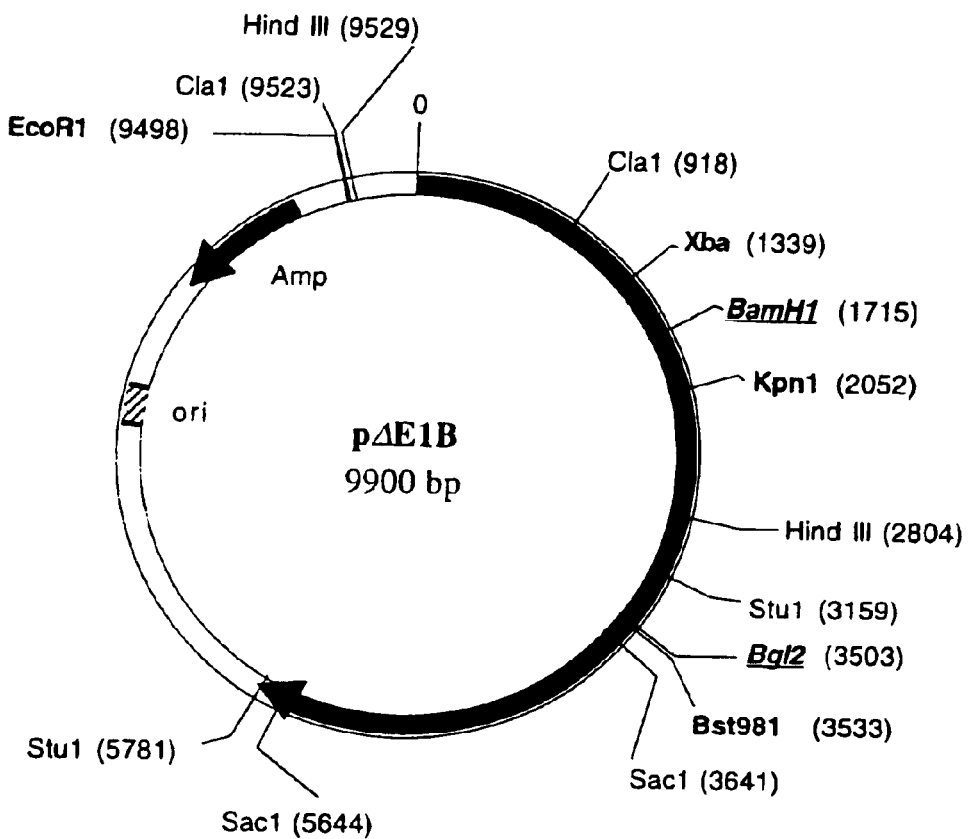
FIG. 2 shows the restriction map of the plasmid pΔE1B.

3. Using Δ55Kmet3'BamHI, a unique Bgl II site was created at nucleotide 3503, upstream of the E1B-55K stop codon, using the Clonetech Advantage Kit and primers:
A5Xba: 5' CCGC$_{1339}$TCTAGAGAATGCAATAGTAGTAC 1361 (SEQ ID NO. 7) Bst981-NC:
5'$_{3552}$TATTCTTTCCCACCCTTAAGCCACGC-CCACACATTTCAGTACC<u>AGATCT</u>GTATC$_{3498}$ (SEQ ID NO. 8)
The Bgl II site is indicated by the bold and underlined portion of the above sequence. The Xba-Bst981 PCR generated fragment, which also contains the mutations introduced by the Stratagene mutagenesis, was reintroduced into the ΔBam/BglpXC1 vector to create the pΔ55K plasmid. The entire XbaI-Bst981 fragment was sequenced to confirm that the mutations were present and limited to only the above mentioned modifications.
This vector can be used to clone in heterologous genes of interest in place of the 55K gene. See FIG. 2.

C. Creation of Vector pΔE1B/pIX.

Vector pΔE1B was further modified to allow for cloning in place of the pIX gene which is downstream from the E1B-55K gene. A unique Swa1 restriction site was created at the stop codon for pIX using Stratagenes' "Quick Change Site-Directed Mutagenisis Kit" and the oligonucleotides:
E1BsaB1-C:
5'$_{4021}$CCCAATGCGATTTAAATCAT-AAATAAAAAACCAGACTCTGTTTG-GATTTGGATCAAGCAAG$_{4077}$ (SEQ ID NO. 9)
E1BsaB1-NC:
5'$_{4085}$ GCAAGACACTTGCTTGATCCAAATC-CAAACAGAGTCTGGTTTTTTATTTAT-GATTTAAATCGCATTGGG$_{4021}$ (SEQ ID NO. 10)

Figure 3:
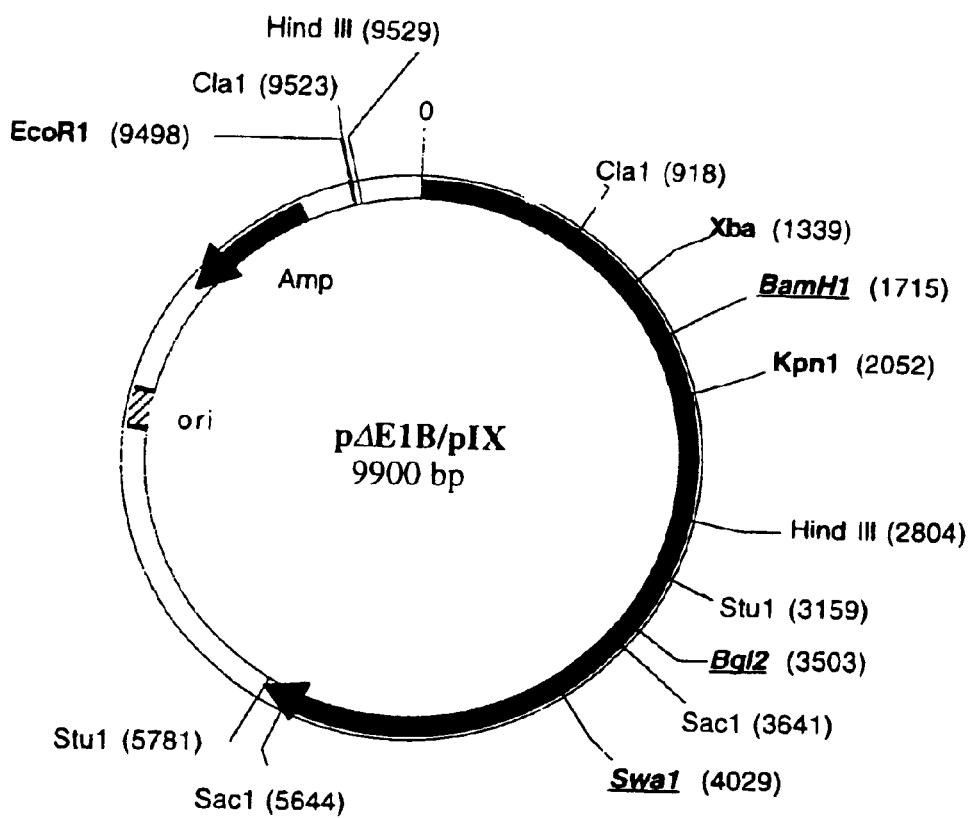
FIG. 3 shows the restriction map of the plasmid pΔE1B/pIX.

The bolded nucleotides in the above sequences represent the changes made to make the Swa1 site. This vector can be used to clone a heterologous gene into the pIX gene only, or into the entire E1B region removing all three genes: 19K, 55K and pix. See FIG. 3.

Example 2

Incorporation of Transgenes into E1B3 Shuttle Vectors

A. pΔE1B/CD.

The *E. coli* cytosine deaminase (CD) gene from the plasmid pCD2 (ATCC Accession #40999) was modified to remove the Nde1 site. A conservative mutation was introduced to change the restriction site without changing the coding sequence of the protein. This was done using PCR-based mutagenesis to cause a T to C change. Additionally, the bacterial initiation site, GCG was changed to the mammalian site, ATG. The CD gene was amplified using Stratagene Pfu DNA Polymerase (Catalog #600154) and the following primers:
CD Bam:
5' GCGCGGATCC$_{1629}$ GTGGAGGCTAACAATGTC-GAATAACGC$_{1655}$ (SEQ ID NO. 11)
CD Swa:
5' GTGAGCATTTAAAT$_{2932}$ CAGTCGTTCAACGTTTG-TAATC$_{2911}$ (SEQ ID NO. 12)

Figure 4:
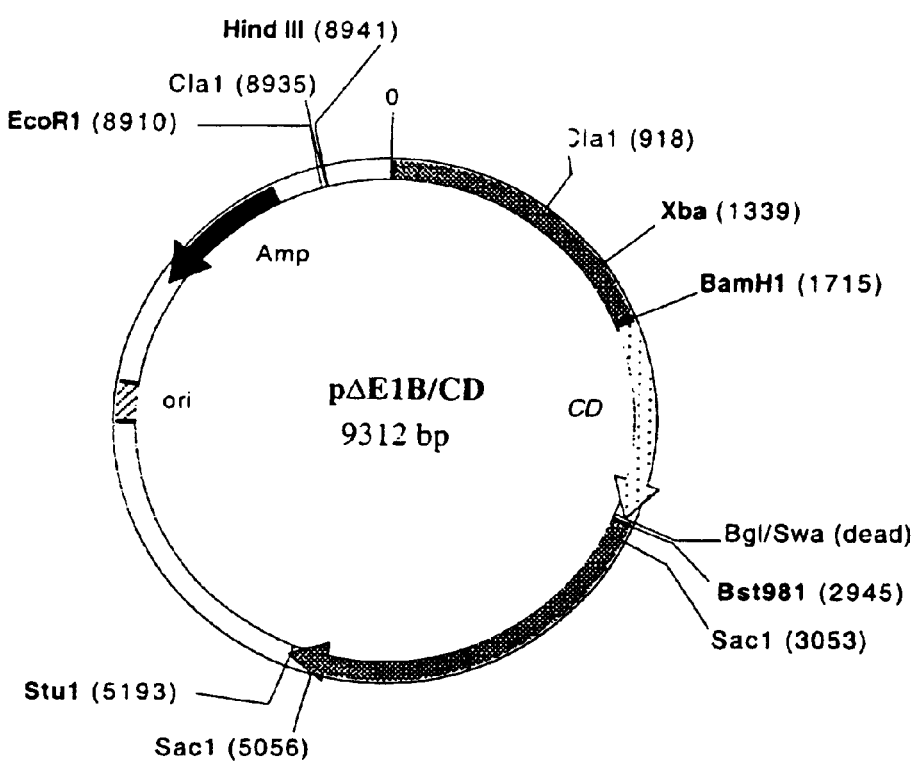
FIG. 4 shows the restriction map of the plasmid pΔE1B/CD.

The bolded portions of the sequences indicate the restriction sites and are not part of the CD gene. The PCR product was digested with BamHI and Swa1 restriction enzymes and gel purified using Qiagens' QIA quick gel extraction kit, according to the manufacturer's instructions The pΔE1B shuttle vector was cut with BamHI following a BglII restriction digest and fill in reaction with T4 DNA polymerase, as described above. The digested vector was gel purified as mentioned. The Bam-Swa CD fragment was ligated into the prepared E1B shuttle vector using standard cloning procedures to create pΔE1B/CD. The pΔE1B/CD construct was sequenced to confirm the insertion of CD. See FIG. 4.

B. Creation of Vector pΔ55K/CD.

Figure 5:
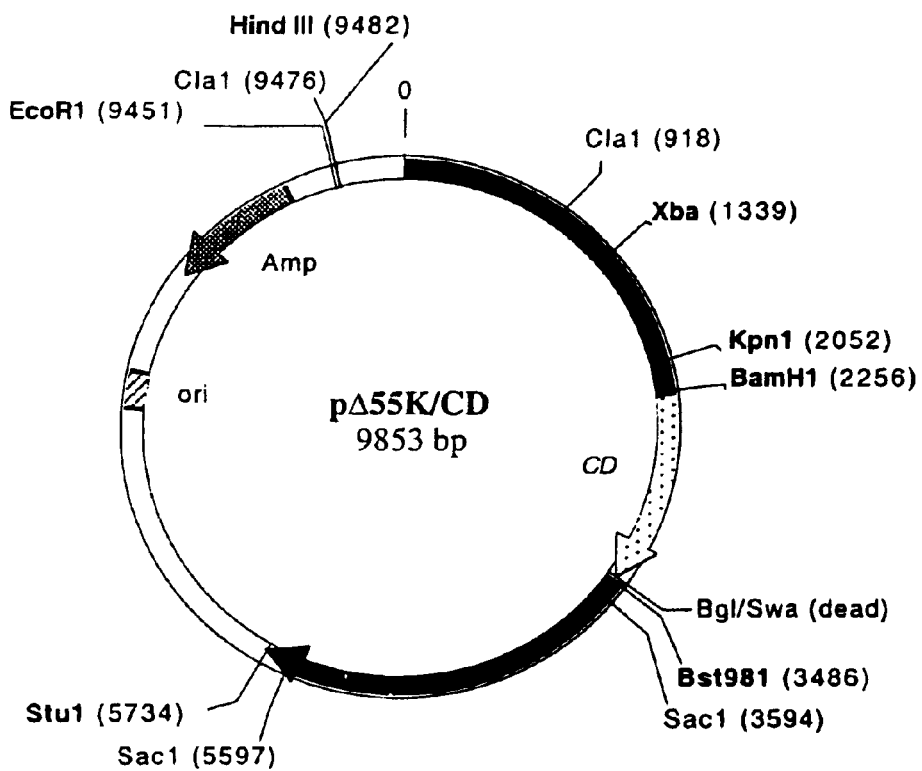
FIG. 5 shows the restriction map of the plasmid pΔ55K/CD.

The BamHI-Swa CD fragment described above was cloned into the pΔ55K shuttle vector which was prepared with Bgl II and BamHI the same way as the pΔE1B shuttle vector, to create the pΔ55K/CD plasmid. The pΔ55K/CD construct was sequenced to confirm the CD insertion. See FIG. 5.

Example 3

Production of ΔE1B/CD and Δ55K/CD Viruses 293 cells were cotransfected with the CD constructs pΔE1B/CD or pΔ55K/CD and the adenovirus right end vector pJM17 (obtainable from Microbix Biosystems, Toronto, Canada) using the standard calcium phosphate procedure as described in McGrory W. J. et al., Virology vol. 163, pages 614–617 (1988). See, also the Microbix Biosystems technical description "Gene Transfer with Adenovirus Vectors." Plaques corresponding to ΔE1B/CD or Δ55K/CD were picked and screened for the CD gene using standard PCR and enzyme restriction digests.

Example 4

Cytosine Deaminase Production Assay

Figure 6:
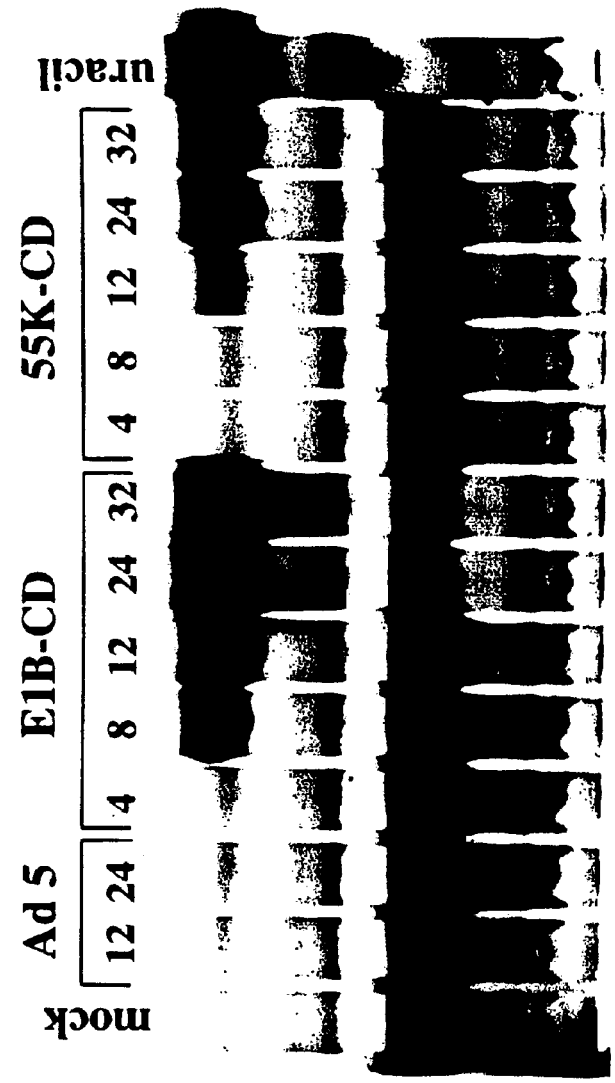
FIG. 6 shows thin layer chromatographic analysis for cytosine deaminase activity from recombinant adenovirus infected A549 cell lysates. The lysates were prepared at the specified times after the cells were infected with the following viruses: Ad5, E1B/CD, and 55K/CD.

The production of functional cytosine deaminase was tested using the methods described by Rogulski et. al., Human Gene Ther., vol. 8 (1) pages 73–85 (1997). In brief, 2–4 million A549 cells in 10 cm dishes were infected at a moi of 10. Cells were infected in 2 mls of DME plus 2% FBS and incubated for one hour at 37° C. and 5% $CO_2$. After one hour, 8 mls of media was added and cells were harvested at 4, 8, 12 and 24 hours post infection. Cell lysates were prepared and 10 ug of extract and 5 mM of [$^{14}$C]cytosine in 20 ul volume were incubated at 37° C. for 45 minutes. Reactions were terminated by the addition of 20 ul of a mixture of cold cytosine and uracil (0.4 mg/ml each). Ten microliter samples were spotted onto a thin layer chromatography sheet (Baker #7009-04) and run in a 1-butanol/water mixture(86%/14%) until the front was near the top. The results of the thin layer chromatography are shown in FIG. 6. It is clear that both ΔE1B/CD and Δ55K/CD express CD.

Example 5

RNA/Northern Blot Analyses

Figure 7A:
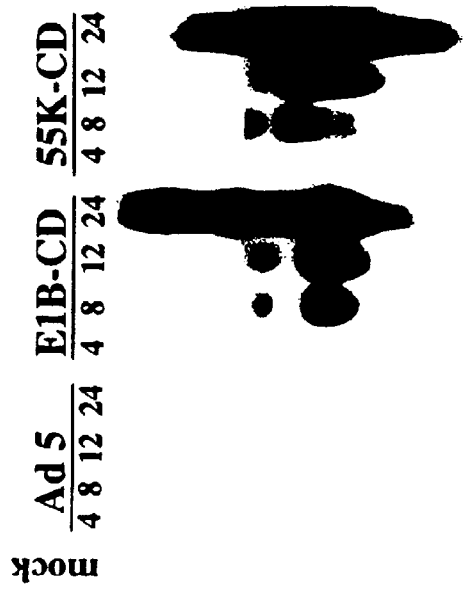
FIG. 7a shows northern analysis for CD RNA prepared from A549 cell lysates. The lysates were prepared and probed with a CD radiolabeled probe at the specified times after the cells were infected with the following viruses: Ad5, E1B/CD, and 55K/CD.

A549 cells were infected with the CD viruses, ΔE1B/CD and Δ55K/CD, and AD5 as described in the CD assay above. RNA was made from the cell pellets using Gibco/BRL reagent Trizol, following the recommended protocol. 10 ug of RNA from each sample was run on a 1% formaldehyde/agarose gel. RNA was transferred to Hybond-N membrane (Amersham) using the standard Northern blot procedures. The blot was probed with a gel purified BamHI-Bst981 fragment of CD, that was radiolabeled using the Amersham Redi Prime kit. The radiographic results are shown in FIG. 7a. It is clear that AD5 alone does not express message for CD, whereas both CD containing viruses do.

Figure 7B:
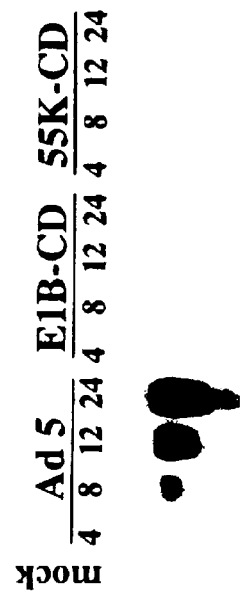
FIG. 7b shows northern analysis for adenoviral 55K RNA prepared from A549 cell lysates. The blots used to test for CD RNA (FIG. 7a) were reused here. The blots were stripped and re-probed with a radiolabeled 55K specific probe.

The blot used in the experiment described above was stripped after exposure to film and re-probed with an adenovirus 55K specific probe, also made using the Amersham Redi Prime labelling kit. The results are shown in FIG. 7b. As expected, only AD5 is positive for 55K message, whereas the two CD containing viruses are not.

Example 6

Creation of pΔKmTNF

The murine gene that encodes tumor necrosis factor (mTNF) was inserted into pΔ55K (See, FIG. 1) to create pΔKmTNF. The murine tumor necrosis factor (mTNF) gene was obtained from a plasmid on deposit with the American Type Culture Collection (ATCC #63169). See also, U.S. Pat. Nos. 4,677,063, and 4,879,226. This plasmid contains the entire mTNF gene including the coding region for the pro-sequence. The entire mTNF gene spans 135bp to 860 bp. As described in U.S. patent application Ser. No. 00/290,732, filed Apr. 13, 1999, the sequence was PCR amplified and cloned into a vector termed pG-mTNFBamSwa. To simplify construction of pΔKmTNF, pG-mTNFBamSwa was the source of the mTNF gene.

Figure 8:
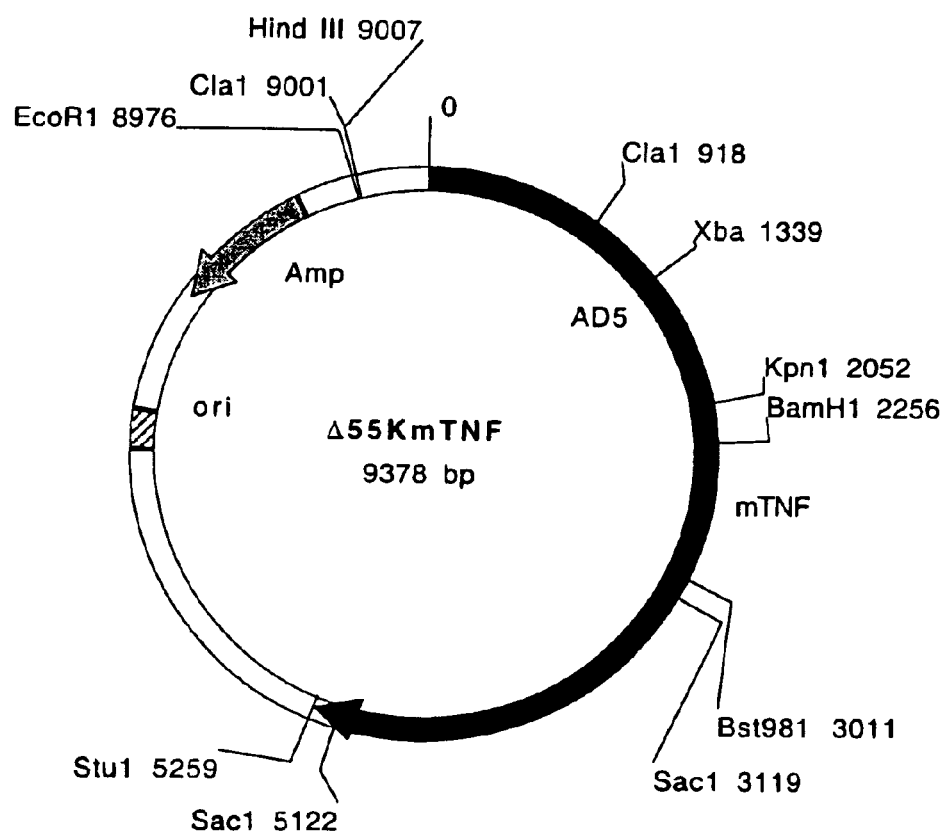
FIG. 8 shows the restriction map of the plasmid pΔKmTNF.

Briefly, pΔKmTNF was prepared by excising the mTNF gene from pG-mTNFBamSwa with BamHI and Swa I, and inserting it into pΔ55K which had been cut with BamHI/BglII, and the BglII site blunt ended to create pΔKmTNF. The plasmid is shown in FIG. 8.

Example 7

Production of TNF Virus 293 cells were cotransfected with the mTNF construct pΔKmTNF and the adenovirus right end vector pJM17 (obtainable from Microbix Biosystems, Toronto, Canada) using the standard calcium phosphate procedure as described in McGrory W. J. et al., Virology vol. 163, pages 614–617 (1988). See, also the Microbix Biosystems technical description "Gene Transfer with Adenovirus Vectors." Plaques corresponding to ΔKmTNF were picked and screened for the mTNF gene using standard PCR and enzyme restriction digests.

Example 8

TNF Assay

Figure 9:
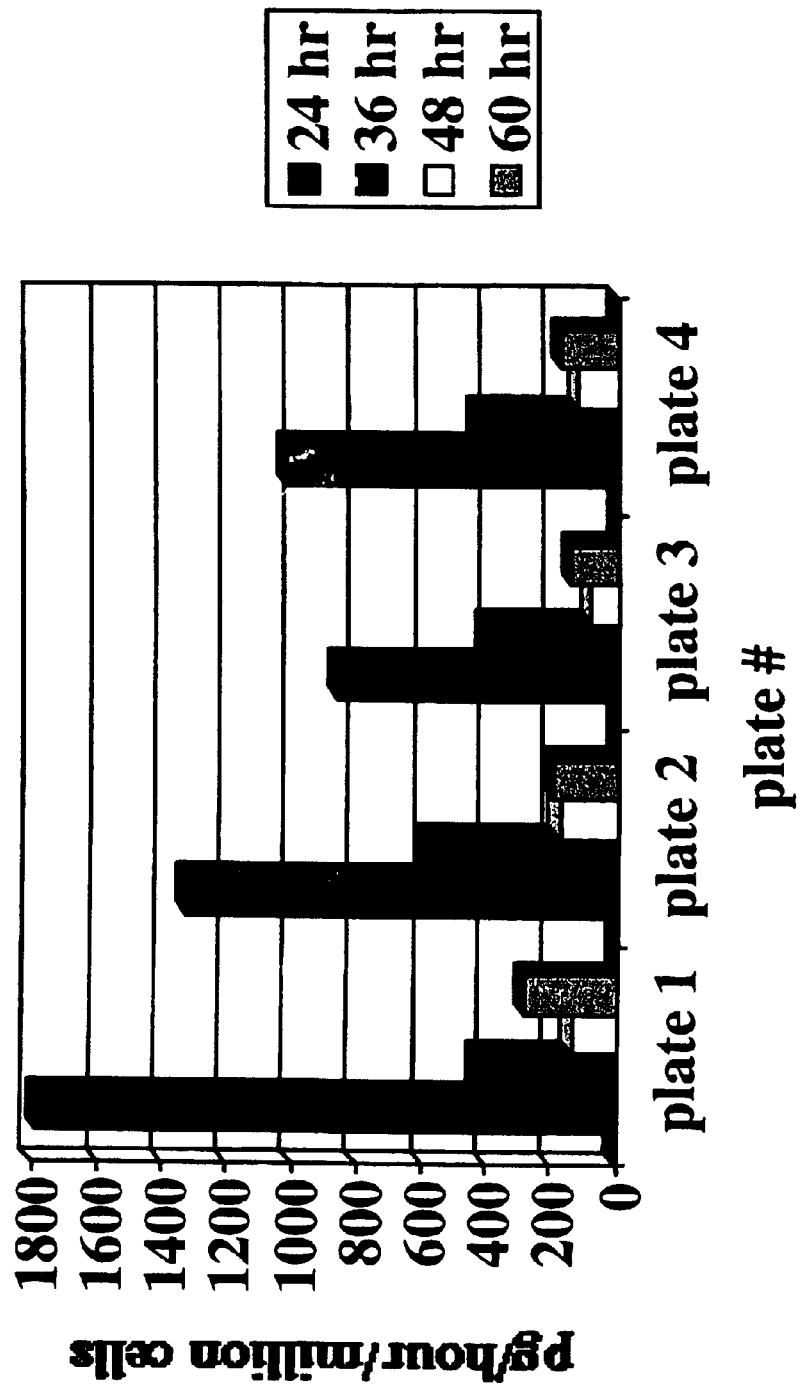
FIG. 9 shows mTNF production in 293 cells infected with pΔKmTNF and assayed at different times.

The A549 cells were plated onto 6 cm plates so that they would be approximately 80% confluent for the infection. The infection with ΔKmTNF was performed as described at an M.O.I. of 10. At various time points, the medium was removed and replaced with 3 ml of fresh DME/2% FBS. This was incubated at 37° C. for one hour. After that interval, a one ml aliquot of the medium was removed and stored frozen at −80° C. until all samples were collected. The medium was replaced on each plate so the final volume was 4 ml until the next time point. The mTNF that was secreted into the medium was assayed using a commercial ELISA assay kit obtained from Biosource, #KMC3012. The assay was conducted according to the manufacturer's instructions. Each sample was determined in duplicate and each time point was collected from 4 different plates of infected cells. FIG. 9 shows the results for 4 6 cm plates at different times. It is apparent that mTNF production occurred in all 4 plates and that the production was highest at the earliest time point, 24 hours, and subsequently declined over 60 hours.

Figure 10:
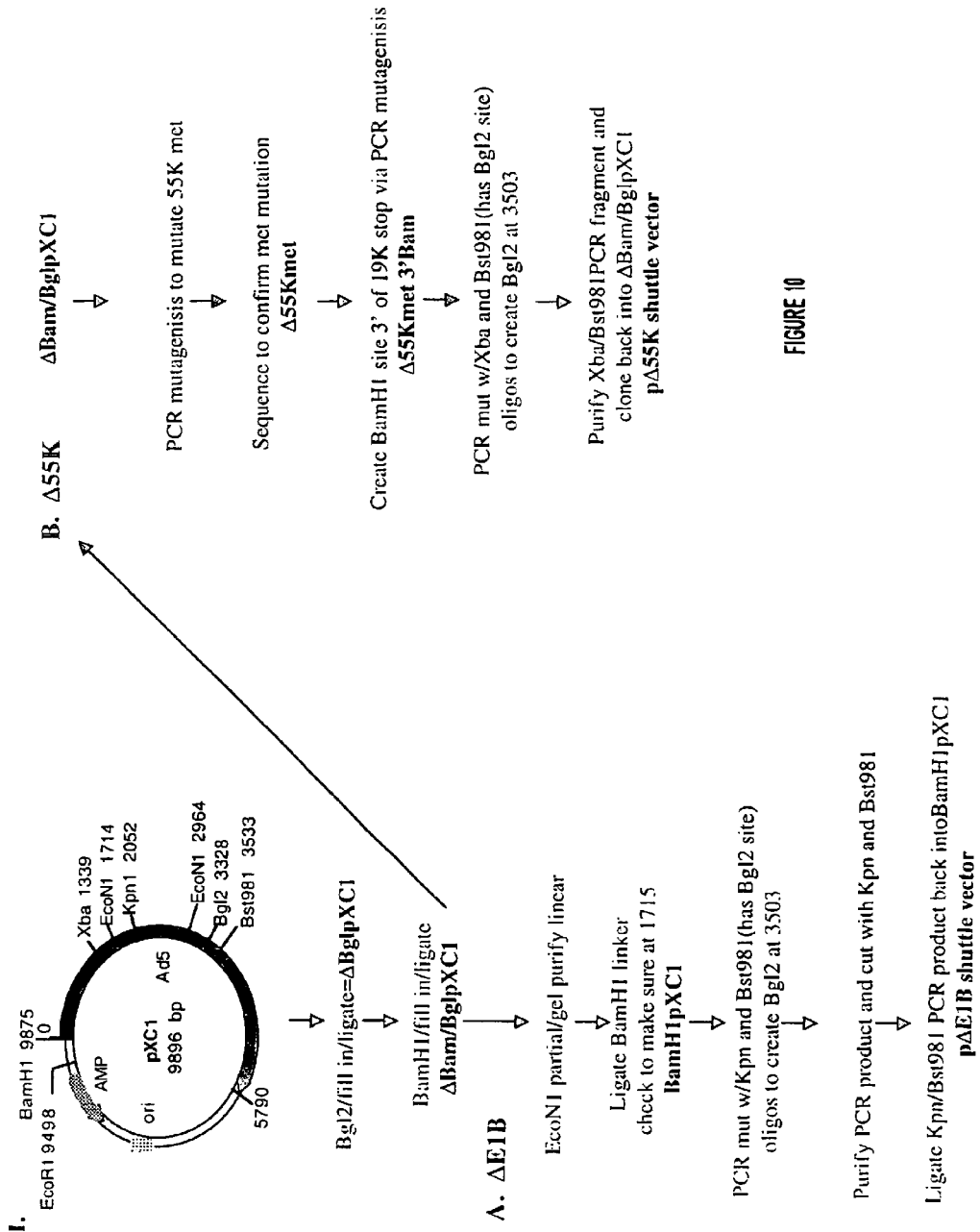
FIG. 10 shows in diagrammatic form the generation of the E1B invention shuttle vectors.

FIG. 10 shows diagrammatically the construction of the E1B shuttle vectors of the instant invention.

The invention now being fully described, it will be apparent to one of ordinary skill in the art that many changes and modifications can be made thereto without departing from the spirit or scope of the appended claims.

---

We claim:

1. A recombinant adenoviral vector comprising a deletion in the E1b region, said deletion comprising at least a portion of the E1b 55K region gene and an E1b region gene selected from the group consisting of p19 or pIX, but retaining the E1b promoter, and substituting for said deletion a heterologous gene such that the heterologous gene has a similar temporal expression pattern as the deleted E1b region gene, and said heterologous gene having the further property of encoding a protein that has anti-tumor activity and that is operably linked to said E1b promoter.

2. The adenoviral vector as described in claim 1 wherein said deletion of said E1b region gene consists of said p19 gene.

3. The adenoviral vector as described in claim 1 wherein said deletion of said E1b region gene consists of the p19 and pIX genes.

4. The adenoviral vector as described in claim 1 wherein said deletion in the E1b region further comprises E1b 55K, p19, and pIX genes.

5. A recombinant adenoviral vector selected from the group consisting of ΔKmTNF, ΔE1B/CD and Δ55K/CD.

6. The recombinant adenoviral vector as described in claim 1 wherein said heterologous gene encodes a protein selected from the group consisting of tumor necrosis factor alpha, interferon gamma, an interleukin, a cell suicide protein, cytosine deaminase, thymidine kinase and mip-3.

7. Cells comprising said adenoviral vector of claim 1.

8. Cells comprising said adenoviral vector of claim 5.

9. Cells comprising said adenoviral vector of claim 6.

10. A method for directly treating a mammal's neoplastic condition in a mammal in need of said treatment, comprising administering to said mammal a therapeutically effective dose of said adenoviral vector of claims 1, 5, or 6.

11. The method as described in claim 10 further comprising administering with said adenoviral vector a chemotherapeutic or an immunosuppressive agent.

12. A replication competent, recombinant adenovirus selected from the group consisting of ΔKmTNF, ΔE1B/CD and Δ55K/CD.

13. A recombinant plasmid selected from the group consisting of pΔKmTNF, pΔE1B/CD, and pΔ55K/CD.

14. A recombinant plasmid selected from the group consisting of pΔE1B, pΔE1B/55K, and pΔE1B/pIX.

* * * * *